United States Patent [19]

Spielmann et al.

[11] 4,266,066

[45] May 5, 1981

[54] PROCESS FOR THE MANUFACTURE OF KETONES

[75] Inventors: Werner Spielmann, Kelkheim; Georg Schaeffer, Hofheim am Taunus, both of Fed. Rep. of Germany

[73] Assignee: Hoechst AG., Frankfurt am Main, Fed. Rep. of Germany

[21] Appl. No.: 97,792

[22] Filed: Nov. 26, 1979 (Under 37 CFR 1.47)

[30] Foreign Application Priority Data

Nov. 28, 1978 [DE] Fed. Rep. of Germany ....... 2851371
Oct. 12, 1979 [DE] Fed. Rep. of Germany ....... 2941391

[51] Int. Cl.$^3$ ................. C07D 333/16; C07D 307/12; C07C 45/00
[52] U.S. Cl. .................................... 549/64; 260/347.8; 568/323; 568/335; 568/407
[58] Field of Search .................. 260/586 R, 347.8; 549/64; 568/323, 335, 407

[56] References Cited

PUBLICATIONS

Tenside, 4, 167–171 (1967).

Organometallic Chemical Reviews A, pp. 47–136 (1968).
Houben–Weyl, vol. VII/2a, 4th ed., Ketone, Part I, pp. 573–575 (1973).
Chem. Abst., vol. 59, 8640(d) (1963).
Chem. Abst., vol. 59, 8640(e) (1963).
Chem. Abst., vol. 60, 14420(c) (1964).

*Primary Examiner*—Alan Siegel
*Attorney, Agent, or Firm*—Curtis, Morris & Safford

[57] ABSTRACT

Ketones are prepared by reacting carboxylic acid halides, in particular carboxylic acid chlorides, with aluminum-alkyl compounds, optionally in the presence of an aluminum trihalide, in methylene chloride as the solvent, at a temperature between about 20° and about 100° C., preferably between about 30° and about 60° C., more preferably of about 40° C. which is the reflux temperature of the methylene chloride. When operating at a temperature above approximately 40° C., pressure higher than atmospheric is applied. The reaction mixture is worked up in usual manner, suitably by decomposition with water followed by distillation.

26 Claims, No Drawings

PROCESS FOR THE MANUFACTURE OF KETONES

Ketones are valuable intermediates and final products in a number of important fields, for example in the dyestuff field, in plant protection, in the pharmaceutical field and in the field of solvents.

A number of classical methods is known for the manufacture of ketones. A recent method starts from carboxylic acid halides, and comprises reacting these compounds with alumino-organic compounds (Al-alkyls and alkyl-Al-halides) to yield the corresponding ketones.

The solvent used originally for this reaction, carried out at a temperature up to 80° C., was benzene [J.Am.-Chem.Soc. 73, 2854–56 (1951)]. This method is reported to give relatively high ketone yields; however, it could not be avoided that Friedel-Crafts acylations of the solvent, namely benzene, took place owing to the catalytical action of the Al compounds used, these reaction involving considerable losses of yield and possibly difficulties in separating and purifying the desired ketone.

To prevent Friedel-Crafts acylations of the solvent, benzene has been replaced by aliphatic hydrocarbons (pentane, hexane etc.) [Fette-Seifen-Anstrichmittel 64, 881–86 (1962)]. In this case the reaction temperature should not be substantially higher than 0° C., otherwise the yield of the desired ketone would drop owing to the increased formation of by-products.

In further testing of solvents, methylene chloride $CH_2Cl_2$ was found to be the most appropriate one [Tenside 4, 167–71 (1967); Organometallic Chemical Reviews A, pages 47–136, in particular pages 55/56 (1968); Houben-Weyl, vol. VII/2a, 4th edition, Ketone, part I, pages 573–575 (1973)]. This solvent is superior over the above-mentioned aromatic and aliphatic hydrocarbons in that practically all reaction partners and final products are soluble therein. When using methylene chloride, the reaction temperature should not be higher than about 0° C., and if possible even lower, since undesired secondary reactions take place increasingly at a temperature above 0° C. and since the yield of the desired ketone is reduced as has been described repeatedly in the relevant literature.

According to the relevant state of the art there was a clear prejudice against performing the known ketone synthesis from carboxylic acid halides and Al-organic compounds in $CH_2Cl_2$ at a temperature above approximately 0° C., otherwise a considerable reduction in yield would have to be taken into account. On the other hand considerable expenditure on cooling is required in order to maintain the required low reaction temperatures because the reaction is exothermal. Thus it is desirable and moreover it was an objective of the instant invention to improve the above-described method which proceeds in relatively satisfactory manner and gives good yields and by which it is possible to obtain ketones that are generally difficult to obtain or not at all obtainable, and to render this method as economic as possible.

This objective could be reached in accordance with the present invention in simple and elegant manner by performing the reaction in question at a temperature at which the heat dissipation can be realized in far more economical manner, i.e. at a temperature in the range of from approximately 20° to approximately 100° C. Surprisingly diminished yields, as compared to working at a temperature of or below 0° C., which had been forecast by the relevant literature, cannot be observed or the yields are reduced to a negligible degree only. In many cases a considerable improvement of the yield could even be observed. Hence a clear technical prejudice has been surmounted by the present invention and simultaneously a known process has been rendered more appropriate and economic.

It is therefore an objective of the present invention to provide a process for the manufacture of ketones by reacting carboxylic acid halides with Al-alkyls or alkyl-Al-halides optionally in the presence of an aluminum halide in $CH_2Cl_2$ as the solvent, and by decomposing the ketone complex formed with water, which comprises carrying out the reaction at a temperature of from about 20° to about 100° C., preferably of from about 30° to about 60° C. and in particular of about 40° C., this latter temperature being the reflux temperature of the boiling $CH_2Cl_2$, optionally under a pressure higher than atmospheric.

The process is suitable for preparing any kind of ketones with the only prerequisite being that the starting carboxylic acid halides contain no further functional groups capable of reacting with Al-alkyls or alkyl-Al-halides in undesired manner. The carboxylic acid halides may be of aliphatic, aromatic, araliphatic or heterocyclic nature and they may contain one or several acid halide groupings. Preferred carboxylic acid halides are those represented by the general formula

in which
$R^1$ is (a) a saturated or unsaturated, branched or linear aliphatic radical, having preferably from 4 to 20, in particular from 4 to 8 carbon atoms;

(b) aryl optionally substituted once or several times, preferably phenyl; in case that aryl or phenyl is substituted, one or two substituents are preferred, these substituents being mainly $C_{1-4}$ alkyl radicals and in particular $CH_3$, alkoxy and in particular $C_{1-4}$ alkoxy, aryloxy and in particular phenoxy, optionally substiuted once or twice such as by aryl or halogen and in particular Cl or Br, $NO_2$, COOR' with R' being $C_{1-4}$ alkyl, preferably $CH_3$, sulfamoyl $SO_2NR'''$ or $SO_2NR''R'''$ with R'' and R''' being organic radicals etc., (c) aralkyl whose aromatic moiety preferably is phenyl and which radical can be substituted analogously to aryl as set forth in subparagraph (b) and whose aliphatic moiety preferably has from 1 to 3 carbon atoms, or (d) a heterocyclic, preferably O- and/or S-containing, radical, in particular furyl or thienyl, and X is halogen, such as chlorine, bromine or iodine, preferably chlorine.

Examples of suitable starting carboxylic acid halides are listed hereinunder:
n-butyryl chloride
n-octadecanoic acid chloride
3,3-dimethylacrylic acid chloride
benzoyl chloride
3-methoxybenzoyl chloride
3-phenoxybenzoyl chloride
o-chlorobenzoyl chloride
p-chlorobenzoyl chloride
3-chloro-5-methylbenzoyl chloride 2,6-dichlorobenzoyl chloride
m-bromobenzoyl chloride
p-bromobenzoyl chloride
p-methylbenzoyl chloride
p-tert.butyl-benzoyl chloride
m-nitrobenzoyl chloride
p-carbomethoxybenzoyl chloride
m-carbobutoxybenzoyl chloride
phenylacetic acid chloride
4-chlorophenylacetic acid chloride
cinnamic acid chloride
4-chlorocinnamic acid chloride
furan-2-carboxylic acid chloride
thiophene-2-carboxylic acid chloride, etc.

For the reaction with the carboxylic acid halides according to the process of the invention there are used Al-alkyls and alkyl-Al-halides of the formula $$R_n^2 AlX_{3-n}$$

in which

R$^2$ is saturated branched or linear alkyl, having preferably from 1 to 12, in particular from 1 to 3, carbon atoms:

X is halogen, such as chlorine, bromine or iodine, preferably chlorine and n is 1, 1.5, 2 or 3, preferably 1.5 (Al-sesquihalides).

Examples of compounds represented by the above formula are: methylaluminum dichloride, methylaluminum sesquichloride, dimethylaluminum chloride, trimethylaluminum, ethylaluminum sesquichloride, ethylaluminum sesqui-iodide, tri-n-propylaluminum, tri-n-hexylaluminum, n-hexylaluminum dichloride, n-dodecylaluminum dibromide, etc.

In case the process of the invention is carried out with the use of an aluminum halide in addition to the Al-alkyls or the alkyl-Al-halides, this Al-halide should suitably have the same halogen radical as the alkyl-Al-halide. The preferred alkyl-Al-halides are chlorides and consequently AlCl$_3$ is the preferred aluminum halide.

By using an aluminum halide additionally to the Al-alkyl or alkyl-Al-halide in question, it is intended to take advantage of as many alkyl groups as possible of the Al-alkyl or of the alkyl-Al-halide for the reaction with the corresponding carboxylic acid halide, because the ketones formed in the process of the invention form rather stable complexes with the Al-alkyls and alkyl-Al-halides and thus the alkyl groups of the Al-organic compounds are no longer available for the further reaction with the carboxylic acid halide. Owing to the fact that Al-halides such as AlCl$_3$ are stronger Lewis acids than Al-alkyls and alkyl-Al-halides, they expel the latter from the complex compounds and render them available for the further reaction with the carboxylic acid halides. It is hence preferred to use per equivalent of carboxylic acid halide (an equivalent of a carboxylic acid halide containing only one COX group=1 mol)

(a) about 1 mol of alkyl-Al-dihalide R$^2$AlX$_2$ (and no Al-halide), (b) about ½ mol of dialkyl-Al-halide R$_2^2$AlX + about ½ mol of Al-halide, (c) about ⅔ mol of alkyl-Al-sesquihalide R$_{1.5}^2$AlX$_{1.5}$ + about ⅓ mol of Al-halide or (d) about ⅓ mol of trialkyl-Al R$_3^2$Al + about ⅔ mol of Al-halide, with the Al-organic compound being suitably used in excess of about 5%. Higher excesses do not bring about any advantage. The same applies to the Al-halide.

When the carboxylic acid halides carry substituents such as keto groups that form stable complexes with Al-organic compounds, there is required additionally per substituent one equivalent of Al-organic compound or of Al-halide.

The process is suitably carried out in the following manner: The CH$_2$Cl$_2$ is introduced into the reaction vessel and the Al-halide, if its use is required, is suspended therein. Subsequently, the required quantity of Al-alkyl or alkyl-Al-halide calculated for the batch is added while carefully excluding oxygen. The acid chloride is added to the reaction mixture at such a speed that the starting methylene chloride reflux can be easily monitored. In this case the reaction temperature amounts to approximately 40° C. Upon completion of the addition of the acid chloride, stirring is continued for a short period of time, generally for about 1 hour.

When the acid chloride is added rather slowly, the heat caused by the exothermal reaction may not be sufficient to bring the CH$_2$Cl$_2$ to a boil. In this case the reaction temperature is below 40° C. and it is in the range from room temperature (about 20° C.) to 40° C.

In some cases it may be advantageous to carry out the reaction at a temperature above approximately 40° C. However, in this case operating must be done under elevated pressure using suitably a closed vessel in which the adequate autogenous pressure is established automatically at elevated temperature. The most advantageous operation is performed at normal pressure at the reflux temperature of the CH$_2$Cl$_2$ (about 40° C.).

Upon completion of the reaction, the reaction mixture is supplemented with water to decompose the ketone-Al-halide complex formed, suitably by pouring the reaction mixture into water or onto ice. Due to the heat formed, the CH$_2$Cl$_2$ begins to boil and thus it can be distilled off or be kept refluxing. The desired ketone is recovered in usual manner, for example by distillation, from the reaction batch treated with water.

Hereinafter there are listed examples of ketones obtainalbe or obtained by the process of the invention:
hexanone-3
decanone-4
nonadecan-2-one
mesityl oxide
butyrophenone
propiophenone
3-methoxyacetophenone
3-phenoxyacetophenone
o-chloroacetophenone
o-chloropropiophenone
m-chloroacetophenone
3-chloro-5-methylpropiophenone
2,6-dichloroacetophenone
m-bromopropiophenone
p-bromoacetophenone
p-bromopropiophenone
p-methylacetophenone
p-methylpropiophenone
p-tert.butyl-butyrophenone
p-nitroacetophenone
p-carbomethoxyacetophenone
m-carbobutoxy-butyrophenone
phenylacetone
1-phenylbutanone-2
4-chlorophenylacetophenone 4-chlorobenzalacetone
2-acetylthiophene
2-acetylfuran etc.

In this process the ketone yield is approximately at least as high as in conventional processes involving operating only at a temperature of about 0° C., or preferably below 0° C., in $CH_2Cl_2$. It may even occur in some cases they more economical yields are obtained only when operating at the higher reaction temperature. This was not to be expected at all owing to what had been reported in the relevant literature cited previously and moreover this operating signifies a considerable improvement since the reaction batch need no longer be kept at a temperature of 0° C. or below 0° C. by cooling. The advantages of the process of the invention are listed hereinunder:

(a) Expensive and complicated cooling system need not be used when operating at higher temperature, especially in boiling methylene chloride, at 40° C. at normal pressure or at pressure higher than atmospheric, and the evaporation cooling system, which can be monitored very easily technologically, can be utilized by refluxing the solvent.

(b) Rather inert carboxylic acid chlorides can be converted in a shorter period of time at elevated temperature.

(c) Operating at elevated temperature scarcely carries the danger of formation of concentrations of unreacted reactants that might be critical from the safety point of view, as a consequence of retarded reactions.

The invention will be illustrated in greater detail in the following examples. In the Examples the following method of operating has been used, unless stated otherwise: $CH_2Cl_2$ was placed in the reaction vessel and solid $AlCl_3$ (in anhydrous form) was added thereto and suspended therein. Subsequently the alkyl-Al or the alkyl-Al-halide was added. The carboxylic acid chloride in question was added to the resulting mixture at a speed such that the starting $CH_2Cl_2$ reflux could be monitored. Upon completion of the addition, stirring was continued for 1 hour.

Thereafter the reaction mixture was poured into water with the methylene chloride being caused to boil owing to the exothermal decomposition heat. The batch was further worked up by distillation.

Unless stated otherwise, 0.3 mol portions of carboxylic acid chloride were reacted with 0.1 mol portions of $AlCl_3$ and with 0.21 mol portions of $(CH_3)_{1.5}AlCl_{1.5}$ or of $(C_2H_5)_{1.5}AlCl_{1.5}$, respectively, in about 1 to 10 g portions of $CH_2Cl_2$ per gram of carboxylic acid chloride.

The Comparative Examples listed in the following Table were carried out in analogous manner, except that the reaction batch was constantly kept at a temperature of 0° C. or below 0° C. by exterior cooling. The results are summarized in the following Table.

TABLE

| Starting carboxylic acid halide | Al-alkyl or alkyl-Al-halide | Al-halide | reaction temp. | reaction product ketone | yield (% of the theory) |
|---|---|---|---|---|---|
| (A) aliphatic: | | | | | |
| $CH_3(CH_3)_2COCl$ | $(C_2H_5)_{1.5}AlCl_{1.5}$ | $AlCl_3$ | about 40° C. | $CH_3(CH_2)_2COC_2H_5$ | 95% |
| " | " | " | 0° C. (comp.) | " | 95% |
| " | $(n-C_6H_{13})AlCl_2$ (0.3 Mol) | — | about 40° C. | $CH_3(CH_2)_2COC_6H_{13}$ | 88% |
| $(CH_3)_2C=CH-COCl$ | $(CH_3)_{1.5}AlCl_{1.5}$ | $AlCl_3$ | about 40° C. | $(CH_3)_2C=CH-CO-CH_3$ | 94% |
| " | " | " | 0° C. (comp.) | " | 93% |
| (B) aromatic: | | | | | |
| C₆H₅-COCl | $(CH_3)_{1.5}AlCl_{1.5}$ | $AlCl_3$ | about 40° C. | C₆H₅-CO-CH₃ | 97% |
| " | " | " | 0° C. (comp.) | " | 82% |
| " | $(C_2H_5)_{1.5}AlCl_{1.5}$ | " | about 40° C. | C₆H₅-CO-C₂H₅ | 95% |
| 2-Cl-C₆H₄-COCl | $(CH_3)_{1.5}AlCl_{1.5}$ | $AlCl_3$ | about 40° C. | 2-Cl-C₆H₄-CO-CH₃ | 98% |
| " | " | " | 22-25° C. | " | 95% |
| " | " | " | 60° C./2 bars | " | 96% |
| " | " | " | 0° C. (comp.) | " | 94% |
| " | $(C_2H_5)_{1.5}AlCl_{1.5}$ | " | about 40° C. | 2-Cl-C₆H₄-CO-C₂H₅ | 94% |
| 3-Cl-C₆H₄-COCl | $(CH_3)_{1.5}AlCl_{1.5}$ | $AlCl_3$ | about 40° C. | 3-Cl-C₆H₄-CO-CH₃ | 96% |
| " | $CH_3AlCl_2$ (0.3 Mol) | — | about 40° C. | " | 95% |
| 3-Cl-C₆H₄-COBr | $(CH_3)_2AlBr$ (0.15 Mol) | $AlBr_3$ (0.15 Mol) | about 40° C. | " | 96% |

TABLE-continued

| Starting carboxylic acid halide | Al-alkyl or alkyl-Al-halide | Al-halide | temp. | reaction product ketone | yield (% of the theory) |
|---|---|---|---|---|---|
| 3-chloro-5-methylbenzoyl chloride (COCl with CH₃ and Cl) | $(C_2H_5)_{1.5}AlCl_{1.5}$ | $AlCl_3$ | about 40° C. | 3-chloro-5-methyl-phenyl ethyl ketone ($H_3C$–Ar(Cl)–$CO-C_2H_5$) | 91% |
| 2,6-dichlorobenzoyl chloride | $(CH_3)_{1.5}AlCl_{1.5}$ | $AlCl_3$ | about 40° C. | 2,6-dichloroacetophenone (Ar(Cl,Cl)–$CO-CH_3$) | 96% |
| 3-bromobenzoyl chloride | $(C_2H_5)_{1.5}AlCl_{1.5}$ | $AlCl_3$ | about 40° C. | 3-bromo-phenyl ethyl ketone (Br–Ar–$CO-C_2H_5$) | 95% |
| 3-methoxybenzoyl chloride | $(CH_3)_{1.5}AlCl_{1.5}$ | $AlCl_3$ (0.4 Mol) | about 40° C. | 3-methoxyacetophenone ($COCH_3$ / $OCH_3$) | 89% |
| 4-bromobenzoyl chloride | $(CH_3)_{1.5}AlCl_{1.5}$ | $AlCl_3$ | about 40° C. | $Br$–⟨O⟩–$CO-CH_3$ | 96% |
| " | $(C_2H_5)_{1.5}AlCl_{1.5}$ | " | about 40° C. | $Br$–⟨O⟩–$CO-C_2H_5$ | 92% |
| 4-methylbenzoyl chloride | $(CH_3)_{1.5}AlCl_{1.5}$ | $AlCl_3$ | about 40° C. | $H_3C$–⟨O⟩–$CO-CH_3$ | 98% |
| " | $(C_2H_5)_{1.5}AlCl_{1.5}$ | " | about 40° C. | $H_3C$–⟨O⟩–$CO-C_2H_5$ | 95% |
| 4-nitrobenzoyl chloride | $(CH_3)_{1.5}AlCl_{1.5}$ | $AlCl_3$ | about 40° C. | $O_2N$–⟨O⟩–$COCH_3$ | 41% |
| 4-ethoxycarbonylbenzoyl chloride | $(CH_3)_{1.5}AlCl_{1.5}$ (0.21 Mol) | $AlCl_3$ (0.4 Mol) | about 40° C. | $H_5C_2OOC$–⟨O⟩–$CO-CH_3$ | 72% |
| 3-phenoxybenzoyl chloride | $(CH_3)_{1.5}AlCl_{1.5}$ (0.3 Mol) | — | about 40° C. | 3-phenoxyacetophenone ($COCH_3$ / O-Ph) | 75% |

(C) araliphatic:

| Starting carboxylic acid halide | Al-alkyl or alkyl-Al-halide | Al-halide | temp. | reaction product ketone | yield (% of the theory) |
|---|---|---|---|---|---|
| phenylacetyl chloride ($CH_2COCl$) | $(CH_3)_{1.5}AlCl_{1.5}$ | $AlCl_3$ | about 40° C. | ⟨O⟩–$CH_2-CO-CH_3$ | 86% |
| " | $(C_2H_5)_{1.5}AlCl_{1.5}$ | " | about 40° C. | ⟨O⟩–$CH_2-CO-C_2H_5$ | 84% |
| " | " | " | 0° C. (comp.) | " | 80% |
| 4-chlorophenylacetyl chloride (Cl–Ar–$CH_2-COCl$) | $(CH_3)_{1.5}AlCl_{1.5}$ | $AlCl_3$ | about 40° C. | $Cl$–⟨O⟩–$CH_2-CO-CH_3$ | 85% |
| 4-chlorocinnamoyl chloride (Cl–Ar–$CH=CH-COCl$) | $(CH_3)_{1.5}AlCl_{1.5}$ | $AlCl_3$ | about 40° C. | $Cl$–⟨O⟩–$CH=CHCO-CH_3$ | 88% |

(D) heterocyclic:

| Starting carboxylic acid halide | Al-alkyl or alkyl-Al-halide | Al-halide | reaction temp. | product ketone | yield (% of the theory) |
|---|---|---|---|---|---|
| 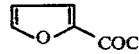 | $(CH_3)_{1.5}AlCl_{1.5}$ (0.21 Mol) | $AlCl_3$ (0.2–0.4 Mol) | about 40° C. | 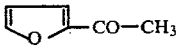 | 75% |
|  | ″ | ″ | 0° C. (comp.) | ″ | 0% |
| 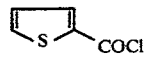 | $(CH_3)_{1.5}AlCl_{1.5}$ (0.21 Mol) | $AlCl_3$ (0.2–0.4 Mol) | about 40° C. | 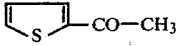 | 88% |
|  | ″ | ″ | 0° C. (comp.) | ″ | 15% |

What is claimed is:

1. A process for the manufacture of a ketone, which comprises reacting a carboxylic acid halide with an Al-alkyl or alkyl-Al-halide, in methylene chloride as solvent, at a temperature of from about 30° to about 60° C., and decomposing the resulting ketone complex with water.

2. A process as defined in claim 1, wherein the reaction occurs in the presence of an aluminum halide.

3. A process as defined in claim 1, wherein the reaction occurs at a temperature of about 40° C.

4. A process as defined in claim 3, wherein the reaction occurs at a pressure higher than atmospheric.

5. The process as defined in claim 1, wherein the carboxylic acid halide is a compound of the formula $R^1COX'$ in which $R^1$ is
(a) a saturated or unsaturated, branched or linear aliphatic radical;
(b) aryl or substituted aryl, said substituted aryl having one or several substituents;
(c) aralkyl or substituted aralkyl, said substituted aralkyl having one or several substituents; or
(d) a heterocyclic radical; and
X' is halogen.

6. A process as defined in claim 5, wherein said aliphatic radical is of from 4 to 20 carbon atoms.

7. A process as defined in claim 6, wherein said aliphatic radical is of from 4 to 8 carbon atoms.

8. A process as defined in claim 5, wherein said aryl is phenyl and said substituted aryl is substituted phenyl.

9. A process as defined in claim 5, wherein said aralkyl is benzyl and said substituted aralkyl is substituted benzyl.

10. A process as defined in claim 5, wherein said heterocyclic radical is an O-, S- or O- and S-containing radical.

11. A process as defined in claim 10, wherein said heterocyclic radical is furyl or thienyl.

12. A process as defined in claim 5, wherein said halogen is chlorine.

13. A process for the manufacture of a ketone, which comprises reacting a carboxylic acid halide with an Al-alkyl or alkyl-Al-halide of the formula $R_n^2AlX_{3-n}$ in which
$R^2$ is saturated or branched linear alkyl;
X is halogen; and
n is 1, 1.5, 2 or 3, in methylene chloride as solvent, at a temperature of from about 30° to about 60° C., and decomposing the resulting ketone complex with water.

14. A process as defined in claim 13, wherein the carboxylic acid halide is a compound of the formula $R^1COX'$ in which $R^1$ is
(a) a saturated or unsaturated, branched or linear aliphatic radical;
(b) aryl or substituted aryl, said substituted aryl having one or several substituents;
(c) aralkyl or substituted aralkyl, said substituted aralkyl having one or several substituents; or
(d) a heterocyclic radical; and
X' is halogen.

15. A process as defined in claim 13 or 14, wherein $R^2$ is alkyl of from 1 to 12 carbon atoms.

16. A process as defined in claim 15, wherein said alkyl is of from 1 to 3 carbon atoms.

17. A process as defined in claim 13 or 14, wherein X is chlorine.

18. A process as defined in claim 13 or 14, wherein n is 1.5.

19. A process as defined in claim 13 or 14, which comprises incorporating, per equivalent of carboxylic acid halide,
(a) about one mol of alkyl-Al-dihalide of the formula $R^2AlX_2$,
(b) about one-half mol of dialkyl-Al-halide of the formula $R_2^2AlX$ and about one-half mol of an Al-halide,
(c) about two-thirds mol of alkyl-Al-sesquihalide of the formula $R_{1.5}^2AlX_{1.5}$ and about one-third mol of an Al-halide, or
(d) about one-third mol of trialkyl-Al of the formula $R_3^2Al$ and about two-third mol of an Al-halide.

20. A process for the manufacture of a ketone, which comprises reacting, in methylene chloride as solvent, a carboxylic acid halide with an alkyl-Al-halide in the presence of an Al-halide, the halogen radical of which is identical to the halogen radical of the alkyl-Al-halide, at a temperature of from about 30° to about 60° C., and decomposing the resulting ketone complex with water.

21. A process as defined in claim 20, wherein the carboxylic acid halide is a compound of the formula $R^1COX'$ in which $R^1$ is
(a) a saturated or unsaturated, branched or linear aliphatic radical;
(b) aryl or substituted aryl, said substituted aryl having one or several substituents;

(c) aralkyl or substituted aralkyl, said substituted aralkyl having one or several substituents; or (d) a heterocyclic radical; and X' is halogen.

22. A process as defined in claim 20 or 21, wherein the Al-halide is $AlCl_3$.

23. A process for the manufacture of a ketone, which comprises reacting a carboxylic acid halide with an Al-alkyl or alkyl-Al-halide, in methylene chloride as solvent, at a temperature of from about 30° to 40° C., and decomposing the resulting ketone complex with water.

24. A process as defined in claim 23, wherein the carboxylic acid halide is a compound of the formula $$R^1COX'$$

in which $R^1$ is (a) a saturated or unsaturated, branched or linear aliphatic radical;

(b) aryl or substituted aryl, said substituted aryl having one or several substituents;

(c) aralkyl or substituted aralkyl, said substituted aralkyl having one or several substituents; or (d) a heterocyclic radical; and X' is halogen.

25. A process for the manufacture of a ketone, which comprises reacting a carboxylic acid halide with an Al-alkyl or alkyl-Al-halide, in methylene chloride as solvent, at a temperature of above about 40° C. at an autogenous pressure higher than atmospheric, and decomposing the resulting ketone complex with water.

26. A process as defined in claim 25, wherein the carboxylic acid halide is a compound of the formula $$R^1COX'$$

in which $R^1$ is (a) a saturated or unsaturated, branched or linear aliphatic radical;

(b) aryl or substituted aryl, said substituted aryl having one or several substituents;

(c) aralkyl or substituted aralkyl, said substituted aralkyl having one or several substituents; or (d) a heterocyclic radical; and X' is halogen.

* * * * *